United States Patent [19]
Turner et al.

[11] Patent Number: 5,835,649
[45] Date of Patent: Nov. 10, 1998

[54] LIGHT DIRECTING AND COLLECTING FIBER OPTIC PROBE

[75] Inventors: Robin Fredrick Bruce Turner; Michael Walter Blades; Lloyd Shane Greek; Hans Georg Schulze, all of Vancouver, Canada

[73] Assignee: The University of British Columbia, Vancouver, Canada

[21] Appl. No.: 867,621

[22] Filed: Jun. 2, 1997

[51] Int. Cl.[6] .................................................. G02B 6/26
[52] U.S. Cl. ........................ 385/31; 250/227.29; 385/12
[58] Field of Search ................................ 385/12, 15, 31; 250/227.28, 227.29, 575, 577

[56] References Cited

U.S. PATENT DOCUMENTS

| | | | |
|---|---|---|---|
| 3,799,150 | 3/1974 | Bonnet | 385/117 X |
| 4,573,761 | 3/1986 | McLachlan et al. | 385/115 |
| 4,725,727 | 2/1988 | Harder et al. | 250/227.28 |
| 4,802,761 | 2/1989 | Bowen et al. | 356/301 |
| 5,253,312 | 10/1993 | Payne et al. | 385/31 |
| 5,257,991 | 11/1993 | Fletcher et al. | 606/17 |
| 5,354,294 | 10/1994 | Chow | 606/16 |
| 5,402,508 | 3/1995 | O'Rourke et al. | 385/31 |
| 5,530,553 | 6/1996 | Hsia et al. | 356/436 |
| 5,582,170 | 12/1996 | Soller | 385/12 X |
| 5,625,459 | 4/1997 | Driver | 385/12 X |
| 5,657,404 | 8/1997 | Buchanan | 385/12 |

*Primary Examiner*—John D. Lee
*Attorney, Agent, or Firm*—C. A. Rowley

[57] ABSTRACT

A fiber-optic probe is formed by a pair of optical fibers one of which delivers light to a target zone and the other collects light from a field of view in the target zone. One of these fibers is provided with a window that opens substantially perpendicular to the longitudinal axis of the fiber and with a transverse surface oriented at an angle to the longitudinal axis of the fiber to reflect light through the window or from the window longitudinally of the axis of this fiber. Two fibers are physically interconnected to position the window on one side of and immediately adjacent to the target zone and the axial end of other fiber to deliver or receive light from another side of the target zone preferably substantially perpendicular to the one side.

25 Claims, 3 Drawing Sheets

LIGHT DIRECTING AND COLLECTING FIBER OPTIC PROBE

FIELD OF INVENTION

The present invention relates to a fiber-optic probe, more particularly, the present invention relates to a fiber-optic probe having fibers in close proximity for delivering and collecting light to and from a target zone and configured to improve the effectiveness of the probe.

BACKGROUND OF THE INVENTION

An optical fiber generally has a core region with a high index of refraction surrounded by a thin cladding region with a lower index of refraction and can guide (transport) light through multiple internal reflections optical fibers are used for a variety of different purposes, for example, for directing light to a particular area or for collecting light from a selected area to which the fiber is aimed. For example, U.S. Pat. No. 5,257,991 issued Nov. 2, 1993 to Fletcher et al. discloses a fiber-optic device for directing light at an angle by providing an optical fiber with a beveled edge.

U.S. Pat. No. 5,354,294 issued Oct. 11, 1994 to Chou describes another fiber-optic device for delivering transmitted radiation at various angles to the central axis of an optical fiber using reflecting surfaces.

None of the above referred to patents teach probes for acquiring chemical physical or other information from within their field of view.

U.S. Pat. No. 5,402,508 issued Mar. 28, 1995 to O'Rourke et al. discloses a probe with improved coupling efficiency. O'Rourke positions two fibers in side by side relationship and utilizes a bevel to redirect the output or input to each of the fibers onto a specific target zone.

U.S. Pat. No. 4,573,761 issued Mar. 4, 1986 to McLachlan et al. shows a plurality of optical fibers for collecting light delivered to the target zone by at least one light delivering fiber. The concept is to direct the light from a delivery fiber and to the collecting fibers to or from the same target zone.

U.S. Pat. No. 4,802,761 issued Feb. 7, 1989 to Bowen et al. describes a method and apparatus for in situ detection or monitoring of selected compounds or gaseous media using RAMAN spectroscopy.

BRIEF DESCRIPTION OF THE PRESENT INVENTION

It is an object of the present invention to provide an improved optical probe particularly suited for spectroscopic investigation of liquid or gaseous samples including liquid or gaseous samples containing suspended or dispersed solid particles.

It is a further object of the present invention to provide an optical probe that improves the delivery or collection of light to or from a target zone.

It is a further object of the present invention to provide an optical probe that may be constructed to improve upon the range of wavelengths and power levels that may effectively be used.

Broadly, the present invention relates to a fiber-optic probe comprising a first optical fiber for delivering light to a target zone, a second optical fiber for collecting light from said target zone, a window in one of said first and second optical fibers, said window facing in a direction substantially perpendicular to a longitudinal axis of said one of said first and second optical fiber, said window being positioned adjacent to one axial end of said one fiber, a reflecting surface at said one axial end of said one fiber and extending across said one fiber at an acute angle to a longitudinal axis of said one fiber to reflect light passing through said one fiber to pass through or be received from said window and means for interconnecting said fibers to position said window along a first side of said target zone and an end of the other of said first and second optical fibers on a second side of said target zone.

Preferably, said first and second sides of said target zone are substantially perpendicular.

Preferably, said window is formed in said second fiber.

Preferably, said first and said second fiber have their longitudinal axes substantially parallel in that portion of said first and second optical fibers immediately adjacent to said target zone.

Preferably, said acute angle is 45°.

Preferably, said window has a field of view determined by the size, shape and position of said window and said reflecting surface and corresponds with an area of said target zone to or from which said light passing longitudinally of said one fiber of said first and second fibers is directed or received.

Preferably said other fiber is said first fiber and said axial end of said first fiber is positioned immediately adjacent to target zone and does not extend into said field of view farther than one half the length of said field of view measured parallel to said longitudinal axis of said first fiber.

Preferably, said first fiber further includes a lens at its axial end adjacent to said target zone for directing light into or collecting light from said target zone according to a specific intensity pattern.

Preferably, said light is ultraviolet light (wavelength less than about 300 nm) and said first fiber is a high efficiency, solarization-resistant ultraviolet light transmitting optical fiber.

Preferably, said cross-sectional area of said second fiber will be significantly larger than the cross-sectional area of said first fiber.

Preferably, said reflecting surface on said second fiber is shaped to enhance the amount of light collected and to concentrate light collection near said longitudinal axis of said second fiber.

Preferably, a pair of said second fibers are arranged to be diametrically opposed relative to said first optical fiber.

Preferably, an anti-reflection coating, suitable for wavelength(s) being used, to reduce losses of light caused by scattering from fiber surfaces is applied to said window and said end.

Preferably, a filter optical coating suitable for the wavelength(s) being used to permit the selective transmission of light of desired wavelength(s) by into said target zone and reduce transmission of light of undesired wavelengths into the target volume and with filter coating, suitable for the wavelength(s) being used, to permit the transmission of light of desired wavelength(s) from the target volume into said second optical fiber and to reduce collection of light of undesired wavelengths from the said target volume.

BRIEF DESCRIPTION OF THE DRAWINGS

Further features, objects and advantages will be evident from the following detailed description of the preferred embodiments of the present invention taken in conjunction with the accompanying drawings in which.

DESCRIPTION OF THE PREFERRED EMBODIMENTS

Figure 1:
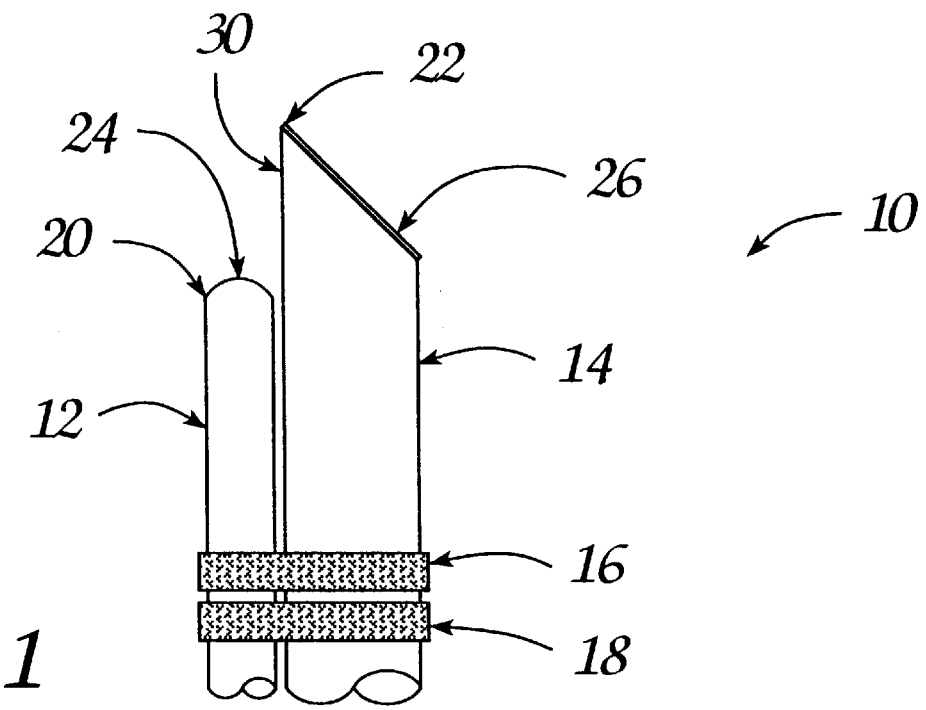
FIG. 1 is a side view of an end of a probe constructed in accordance of the present invention

As shown in FIG. 1, probe 10 of the present invention comprises a pair of optical fibers 12 and 14 interconnected by any suitable means, for example, by adhesive or as illustrated by a pair of bands 16 and 18 to position their ends 20 and 22 in a selected spatial relationship. In the illustrated arrangement, the optical fiber 12 is the delivery fiber and is provided with a lens 24 at its end to direct light into a target zone (a volume of space) 28 at the end of 20 of the optical fiber 12 (or from the target zone into the fiber 20) with a selected intensity pattern. The end 22 is formed with a reflecting surface 26 extending at an angle α to the longitudinal axis to the fiber 14 across the fiber 14. The reflecting surface 26 is shown planar but may be curved or otherwise shaped to yield a selected field of view.

Figure 3:
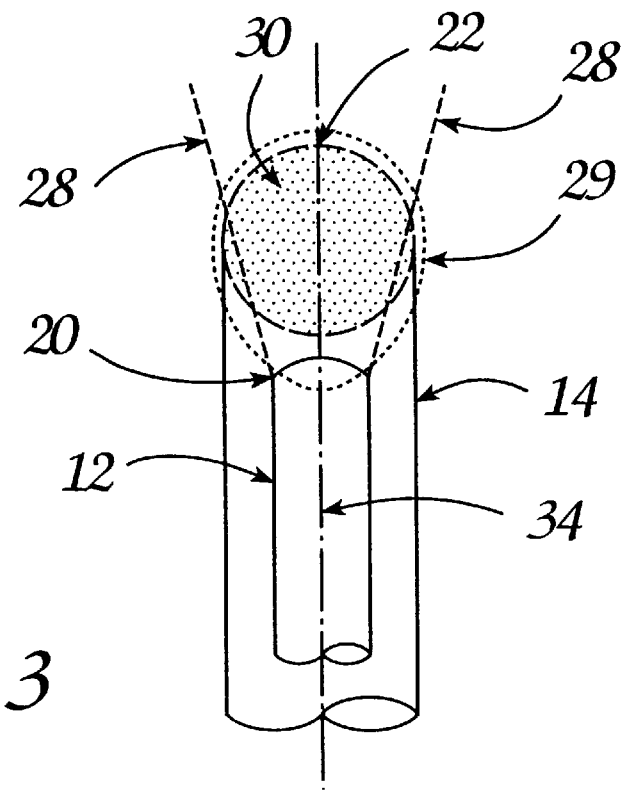
FIG. 3 is a view in the direction of the arrow 3 in FIG. 2 illustrating the target zone and the field of view.

The target zone is generally indicated at 28 i.e. bounded by the dash lines 28 in FIG. 3 (also shown in FIG. 4) and extends as a projection from the end of 20 of fiber 12 of opposite sides of the fiber 12. The target zone 28 is illuminated and light from the target zone in the view of the reflecting surface 26 as schematically represented by the area 29 i.e. bounded by the dash line 29 in FIG. 3 is collected through the window 30 at one end and on the side of the fiber 14 facing the target zone 28 and is reflected by the reflecting surface 26 to pass longitudinally of the fiber 14.

The target zone 28 as above indicated is a target volume defined by the intersection of the field of view (to be further defined below) and the "acceptance cone" of the excitation (light directing) fiber 12 which has the same shape independent of the direction of travel of the light. The symmetrical cone shape indicated in FIG. 3 is due to the indicated symmetry of the lens 24, and illustrated at 28 in FIG. 3, other nonsymmetrical shapes are also useable The field of view 29 of the reflecting surface as is known is determined by the size and shape of the reflecting surface and the angles φ and θ.

The angle θ (see FIG. 4) is the acceptance angle of the fiber, beyond which impinging light rays will not be collected and is defined by $$\theta = \sin^{-1}\left[\frac{\sqrt{n_{co}^2 - n_{cl}^2}}{n_{med}}\right]$$

where $n_{co}$=the refractive index of the core of the fiber, $n_{cl}$32 the refractive index of the cladding of the fiber, and $n_{med}$=the refractive index of the medium exterior to the fiber.

The angle φ is the angle subtended by a light ray which enters the fiber at an angle of incidence θ, is refracted at the interface between the exterior medium and the fiber cladding, is refracted again at the interface between the fiber cladding and the fiber core, and which impinges on the most distant point from the origin of the ray on the reflecting surface 26.

Figure 4:
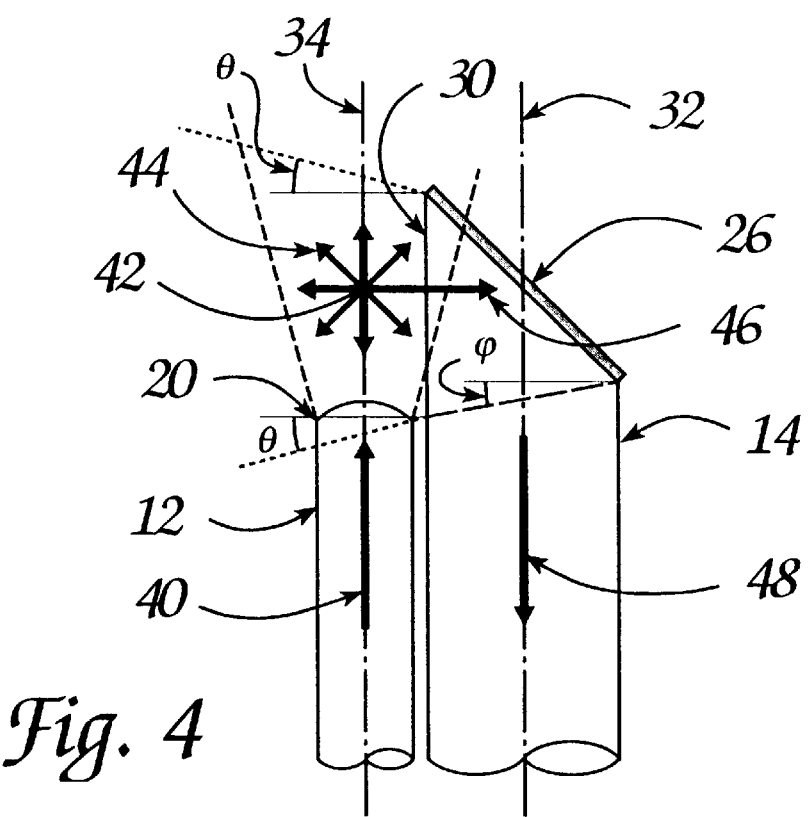
FIG. 4 is a view similar to FIG. 2 illustrating the operation of the present invention.

The actual field of view 29 projects outward from the collection fiber as illustrated in FIG. 4 at angle θ measured from a datum which is perpendicular to, and intersects both axial centerlines 32 and 34. The actual field of view 29 is thus complex and is a function of the distance away from the collecting fiber surface and as above indicated has been roughly shown in section as indicated at 29 in FIG. 3.

It will be apparent that the light collected from the target zone may be reflected light or scattered from (as in RAMAN spectroscopy) from the target zone or generated within the target zone (as in fluorescence or other forms of luminescence) depending on the application.

The fiber 14 is in effect formed with a window 30 that opens into the target zone 28 on the side of the fiber 14 facing the target zone 28, i.e. side of the fiber 14 in the illustrated arrangement closely adjacent to the fiber 12. The light in field of view 29 of the reflecting surface 26 may pass through this window 30.

Figure 2:
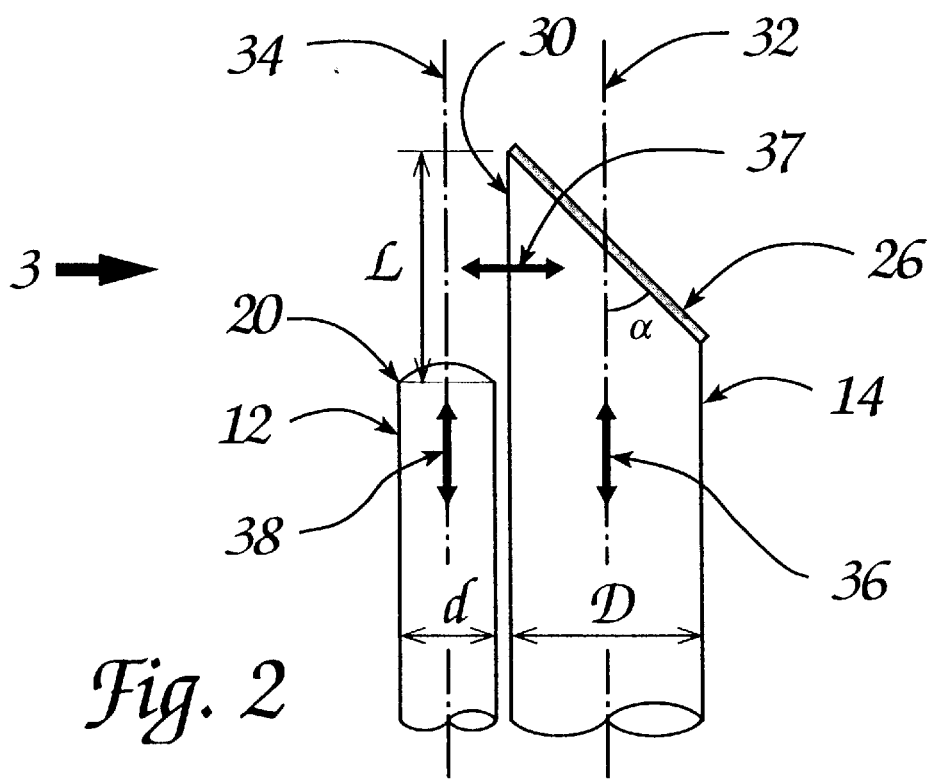
FIG. 2 is an enlarged view of the probe end.

The length L as shown in FIG. 2 defines the distance between the end 20 of the fiber 12 and the end 22 of the fiber 14 farthest from the end 20. This length L in the arrangement illustrated in FIG. 2 (with the fibers 12 and 14 substantially in direct contact) is approximately equivalent to the diameter D of the fiber 14 divided by the tangent of the angle α (the angle of the reflecting surface 26 to the axis 32 of the fiber 14), i.e. L=D/tan α, assuming the reflecting surface 26 extends over the full cross section of the fiber 14. This length L shown in the illustration is a simplified representation of the maximum axial length of the field of view 29 in a direction parallel to the longitudinal axis 32 of the fiber 14 (obviously it is longer at greater distance from the window 30 and is dependent for example in part on angle θ). It is preferred that the end 20 of the fiber 12 approach very close the field of view 29 so the spacing or length L between the end 20 of fiber 12 and the end 22 of fiber 14 will generally not exceed L, however, the length L may be shorter, i.e. the distance L from the end 20 to the end 22 may be reduced and the end of the fiber 12 encroach into the field of view 29 but generally the distance L not will not be less than ½ the length of the field of view measured parallel to the axis 32 i.e. less than about ½ the distance L illustrated in FIG. 2. Such encroachment would reduce significantly the size of the target zone 28 in the field of view 29.

The diameter of the fiber 12 as indicated at d is generally (but not necessarily) less than the diameter D of the fiber 14 when the fiber 12 is the fiber delivering light to the target zone 28 and fiber 14 is the collecting fiber. Generally, the cross-sectional area of the collecting fiber is larger than that of the delivery fiber for example the collecting fiber may have a cross sectional area of about twice that of the delivery fiber.

The fibers 12 and 14 have been described as being substantially circular as this is the most prolific form of such optical fibers. However, it is not essential that these fibers have a circular cross section. They could for example be rectangular or elliptical.

It is preferred that the light be delivered to the target zone 28 using the fiber 12. However, it is also possible to direct the light to the target zone 28 through the window 30, i.e.

from the fiber 14 and reflected by the reflecting surface 26 into field of view 29 of the surface which then defines the target zone and light to be collected from this target zone is transmitted via the fiber 12. This possibility is schematically represented by the two ended arrows 36 and 38 and the fibers 14 and 12 respectively in FIG. 2.

It will be noted that the axial center line 34 of the fiber 12 is substantially parallel to the axial center line of the fiber 14 and that the fibers extend from the target zone 12 in parallel relationship and in the same direction. This is the preferred layout of the present invention, however, it is obviously possible to rearrange the fibers, it being important that the window 30 be at one side of the target zone and the end 20 define another side of the target zone. Preferably, the side defined by the window 30 will in effect be substantially perpendicular to the side defined by the end 20. However, the two longitudinal axes 32 and 34 need not be parallel.

The operation of the probe 10 will now be described using the fiber 12 for delivering light and the fiber 14 for collecting light.

Light is directed as indicated by the arrow 40 into the target zone 28 which is shown as being substantially rectangular although it is likely that the intensity pattern will flare and become wider the greater the distance from the end 20 depending on the shape of the lens 24 and whether or not a lens 24 is used. The lens 24 when used will generally impose a selected intensity pattern on the light that will normally better ensure the light is not impinged directly into the collecting fiber.

The light in the target zone interacts with matter e.g. the sample element or the like 42 in the target zone 28 and within the area of field of view 29. This sample element 42 may emit, scatter or reflect light in all directions (depending on the application) as indicated by the arrows 44 some of which, as indicated by the arrow 46, passes through the window 30 and is reflected by the reflecting surface 26 to direct the light substantially parallel to the longitudinal axis 32 of the fiber 14 as indicated by the arrow 48 and be delivered to the sensing or analyzing equipment (not shown) with which the probe is to be used.

Figure 5:
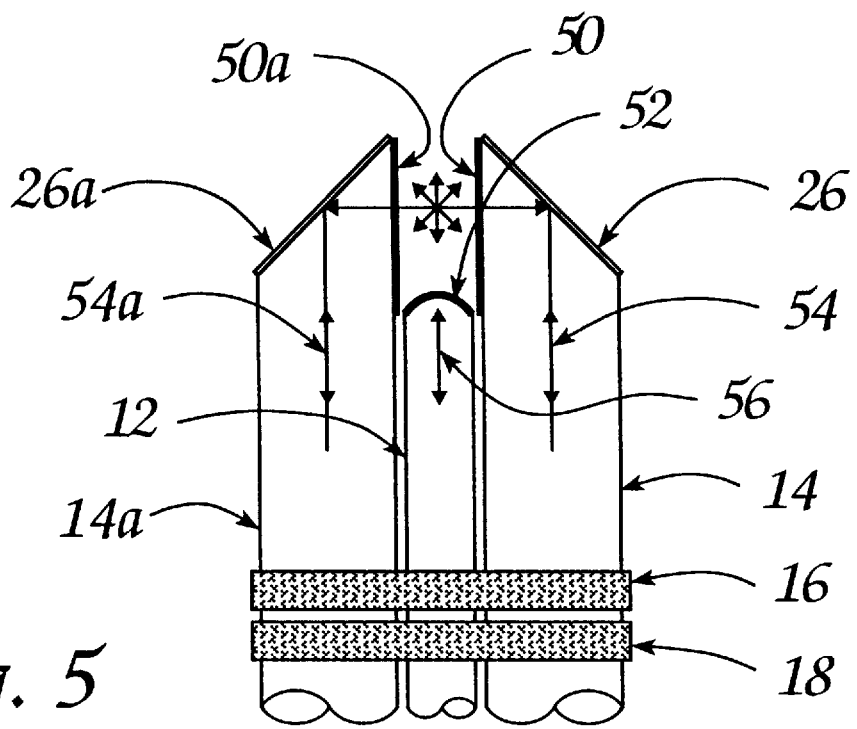
FIG. 5 is a view similar to FIG. 2 of a probe with specific arrangement of a plurality of fibers relative to a central fiber and having an anti reflecting coating through which the light passes.
Figure 6:
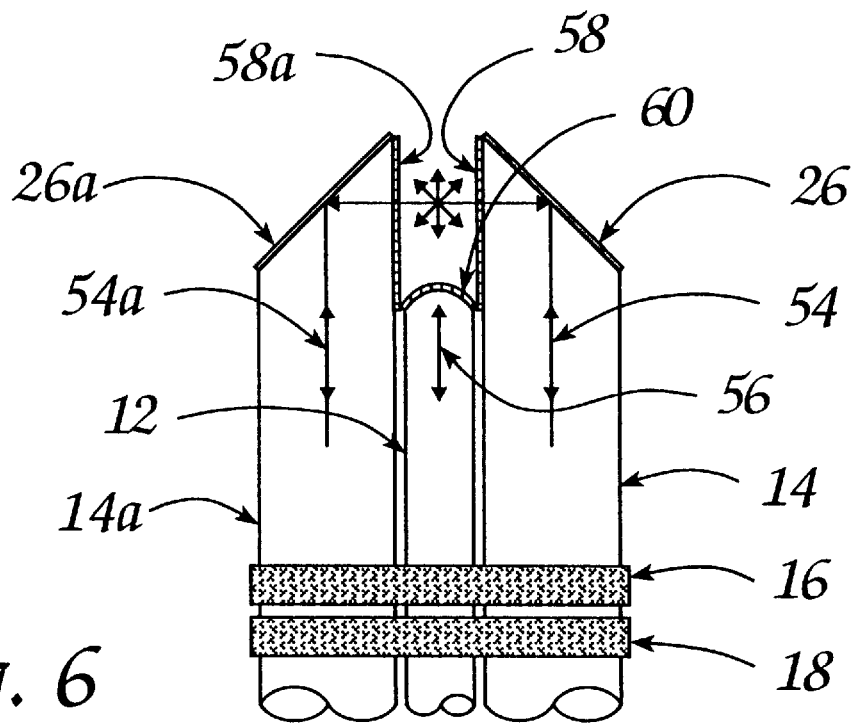
FIG. 6 is a view similar to FIG. 2 but with the anti reflecting coating replaced by a filter.

Turning to FIGS. 5 and 6 these figure illustrate specific arrangements of fibers around a central fiber (fiber 12). Fiber 14 is as described above and carries the same reference numbers and fiber 14a is essentially the same as fiber 14 and thus the elements of fiber 14a carry the same reference characters as their equivalents in fiber 14 but followed by the letter a.

As shown a pair of fibers 14 and 14a are positioned on diagonally opposed sides of the central fiber 12 so that the longitudinal axes of these fibers 12, 14 and 14a are all contained in an axial plane. Thus in the embodiments of FIGS. 5 and 6 the pair of opposed optical fibers 14, 14a can be used either to collect or redirect light emitted, scattered, or otherwise generated from or in transit through the target volume or to deliver light of the same or a different wavelength(s) as that being delivered by said first optical fiber to the target volume.

In the embodiment illustrated in FIG. 5 the ends or windows of the fibers 12, 14 and 14 through which light passes namely, the windows of fiber 14 and 14a and the (lensed) end of fiber 12 are coated with a layer of anti-reflection coating indicated at 50, 50a and 52 respectively. These anti-reflection coatings reduce the reflection losses from the surfaces of the fiber and are thus selected to be suitable for the wavelength range of light being transmitted and/or collected.

The embodiment illustrated in FIG. 6 is similar to that of FIG. 5 and like reference have been used to represent corresponding elements in the two figures. In the FIG. 6 embodiment the coatings 50, 50a and 52a of FIG. 5 have been replace by filters 58, 58a and 60 respectively. Preferably the filters will be formed by coating with a layer of optical material comprising a notch filter suitable for the wavelength(s) of light being transmitted by the optical fibers. The filter optical material on the transmitting fiber has as its purpose the prevention of light of undesired wavelength(s) from being transmitted by into said target zone (target volume) and the receiving fiber is coated with a layer of optical material comprising a filter suitable for the selective transmission of desired wavelength(s) of light being collected by the receiving or collecting optical fiber from the target zone (target volume) i.e. to prevent or reduce the collection of undesirable wavelength(s). Thus filter optical material on the collecting fiber has as its purpose the transmission of light from the said target zone (target volume) into the collecting fiber and the prevention of light of undesired wavelength(s) emitted, scattered, or otherwise generated from within or without said target zone (target volume) from being collected by collecting optical fiber.

FIGS. 5 and 6 shown only a pair of opposed fibers 14 and 14a but a number of different pair may be used in a manner similar to that described above. For some applications the surrounding fibers need not be in opposing pairs.

In the above description, the reflecting surface 26 is being shown as substantially planer. It may also be curved, for example, it could have a convex shape so that the reflected light is concentrated near the axial center line of 32 of the fiber 14.

The angle α has been indicated to be preferably at 45°. However, it may be varied and if the angle of the axis 32 to the adjacent side of the target zone 28 is skewed, it may be desirable to skew the angle α correspondingly so that the reflected light either passes axially of the fiber 14 or if the fiber 14 is being used as the transmitting fiber that the light be directed through the window 30 at the appropriate angle.

In some applications it is preferable to deliver deep ultraviolet light (wavelength less than about 300 nm) to the target zone. In such cases at least the delivery fiber is preferably is formed by a high efficiency, solarization-resistant ultraviolet light transmitting optical fiber such as those sold by Polymicro Technologies Incorporated of Phoenix, Ariz. USA.

While only a pair of side by side fibers have been shown it will be evident that a number of fibers may be clustered together to form the probe. For example a plurality of fibers 14 may be arranged to encircle a single central fiber 12 or any other suitable arrangement of the fibers may be provided.

Having described the invention, modifications will be evident to those skilled in the art without departing from the scope of the invention as defined in the appended claims.

We claim:

1. A fiber-optic probe comprising a first optical fiber for delivering light directly into a target zone, a second optical fiber for collecting light from said target zone, a window in one of said first and second optical fibers, said window facing in a direction substantially perpendicular to a longitudinal axis of said one of said first and second optical fibers, said window being positioned adjacent to one axial end of said one fiber and defining a first side of said target zone, a reflecting surface at said one axial end of said one fiber and extending across said one fiber at an acute angle to a longitudinal axis of said one fiber to reflect light passing through said one fiber to pass through or be received from said window directly into or from said target zone and said first and second fibers are interconnected in fixed relationship with said first and second fibers in intimate side by side relationship with said window defining said first side of said target zone and an axial end of the other of said first and second optical fibers defining a second side of said target zone extending from said first side so that said light passes directly to or from said target zone through said axial end of said other fiber.

2. A fiber-optic probe as defined in claim 1 wherein said window and said axial end are substantially perpendicular so that said first and second sides of said target zone are substantially perpendicular.

3. A fiber-optic probe as defined in claim 2 wherein said window is formed in said second fiber.

4. A fiber-optic probe as defined in claim 3 wherein, said first and said second fibers have their longitudinal axes substantially parallel in that portion of said first and second optical fibers immediately adjacent to said target zone.

5. A fiber-optic probe as defined in claim 4 wherein said acute angle is 45°.

6. A fiber-optic probe as defined in claim 3 wherein said reflecting surface on said second fiber is curved to deflect more light substantially along said longitudinal axis of said second fiber.

7. A fiber-optic probe as defined in claim 2 wherein said window has a field of view determined by the size, shape and position of said reflecting surface and corresponds with an area of said target zone to or from which said light passing longitudinally of said one fiber of said first and second fibers is directed or received.

8. A fiber-optic probe as defined in claim 7 wherein said other fiber is said first fiber and said first and second fibers are interconnected so that said axial end of said first fiber does not extend into said field of view farther than one half the length of said field of view measured parallel to said longitudinal axis of said first fiber.

9. A fiber-optic probe as defined in claim 8 wherein said reflecting surface on said second fiber is shaped to deflect more light substantially along said longitudinal axis of said second fiber.

10. A fiber-optic probe as defined in claim 2 wherein said second optical fiber has a cross-sectional area greater than that of said first fiber.

11. A fiber-optic probe as defined in claim 2 wherein a pair of said second fibers are arranged to be diametrically opposed relative to said first optical fiber.

12. A fiber-optic probe as defined in claim 11 wherein an anti-reflection coating, suitable for wavelength(s) being used, to reduce losses of light caused by scattering from fiber surfaces is applied to said window and said axial end.

13. A fiber-optic probe as defined in claim 11 wherein a filter optical coating suitable for the wavelength(s) being used to permit the selective transmission of light of desired wavelength(s) by into said target zone and reduce transmission of light of undesired wavelengths into the target volume and with filter coating, suitable for the wavelength(s) being used, to permit the transmission of light of desired wavelength(s) from the target volume into said second optical fiber and to reduce collection of light of undesired wavelengths from the said target volume.

14. A fiber-optic probe as defined in claim 2 wherein an anti-reflection coating, suitable for wavelength(s) being used, to reduce losses of light caused by scattering from fiber surfaces is applied to said window and said axial end.

15. A fiber-optic probe as defined in claim 2 wherein a filter optical coating suitable for the wavelength(s) being used to permit the selective transmission of light of desired wavelength(s) by into said target zone and reduce transmission of light of undesired wavelengths into the target volume and with filter coating, suitable for the wavelength(s) being used, to permit the transmission of light of desired wavelength(s) from the target volume into said second optical fiber and to reduce collection of light of undesired wavelengths from the said target volume.

16. A fiber-optic probe as defined in claim 1 wherein said window is formed in said second fiber.

17. A fiber-optic probe as defined in claim 16 wherein, said first and said second fibers have their longitudinal axes substantially parallel in that portion of said first and second optical fibers immediately adjacent to said target zone.

18. A fiber-optic probe as defined in claim 17 wherein said acute angle is 45°.

19. A fiber-optic probe as defined in claim 16 wherein said reflecting surface on said second fiber is curved to deflect more light substantially along said longitudinal axis of said second fiber.

20. A fiber-optic probe as defined in claim 1 wherein said window has a field of view determined by the size, shape and position of said reflecting surface on said window and corresponds with an area of said target zone to or from which said light passing longitudinally of said one fiber of said first and second fibers is directed or received.

21. A fiber-optic probe as defined in claim 20 wherein said other fiber is said first fiber and said first and second fibers are interconnected so that said axial end of said first fiber does not extend into said field of view farther than one half the length of said field of view measured parallel to said longitudinal axis of said first fiber.

22. A fiber-optic probe as defined in claim 21 wherein said reflecting surface on said second fiber is curved to deflect more light substantially along said longitudinal axis of said second fiber.

23. A fiber-optic probe as defined in claim 1 wherein said first fiber further includes a lens at its axial end adjacent to said target zone for directing light into said target zone.

24. A fiber-optic probe as defined in claim 1 wherein said light is deep ultraviolet light and said first fiber is a high efficiency, solarization-resistant ultraviolet light transmitting optical fiber.

25. A fiber-optic probe as defined in claim 1 wherein said second optical fiber has a cross-sectional area greater than that of said first fiber.

* * * * *